United States Patent [19]
Ingram et al.

[11] Patent Number: 5,366,491
[45] Date of Patent: Nov. 22, 1994

[54] MOIST HEAT APPARATUS

[75] Inventors: Aaron N. Ingram, Canton; Mark H. Bruder, Dunwoody, both of Ga.; Eric Flam, East Brunswick, N.J.

[73] Assignee: Bruder Healthcare Company, Marietta, Ga.

[21] Appl. No.: 75,057

[22] Filed: Jun. 10, 1993

[51] Int. Cl.$^5$ ............................................. A61F 7/00
[52] U.S. Cl. .................................... 607/108; 607/114; 383/901; 126/204; 165/46
[58] Field of Search .................... 607/108–112, 607/114, 96; 62/530; 126/204; 165/46; 383/901

[56] References Cited

U.S. PATENT DOCUMENTS

| | | | |
|---|---|---|---|
| 4,325,254 | 4/1982 | Svacina et al. | 607/114 |
| 5,181,905 | 1/1993 | Flam | 602/41 |
| 5,190,033 | 3/1993 | Johnson | 607/114 |
| 5,247,928 | 9/1993 | Stilts, Jr. | 607/114 |

FOREIGN PATENT DOCUMENTS 2257367 1/1993 United Kingdom ................. 383/901

Primary Examiner—Lee S. Cohen
Assistant Examiner—Robert L. Nasser, Jr.
Attorney, Agent, or Firm—Needle & Rosenberg

[57] ABSTRACT

This invention relates to moist heat therapy. More particularly, the invention relates to an improved moist heat pack and method of using the same. The present invention has a temperature monitoring means attached to the outer surface of a moist heat pack that is specifically calibrated to measure skin surface temperature at the opposite outer skin contacting surface. The temperature monitoring device of the present invention thereby provides a means for continuously monitoring skin surface temperature during therapy. The moist heat pack of the present invention can also comprise a means for preventing moisture evaporation from the top surface of the pack.

12 Claims, 1 Drawing Sheet

MOIST HEAT APPARATUS

BACKGROUND OF THE INVENTION

1. Field of the Invention

This invention relates to a moist heat therapy. More particularly, the invention relates to an improved moist heat pack and method of using the same.

2. Background Art

The effective treatment of injuries holds paramount importance in the health-care field. Moist heat therapy is a recommended treatment for many injuries, and utilizes a moist heat pack. To be most effective, such therapy requires both temperature control and moisture retention at the injury site. Maintaining an optimum range of temperature of the heat pack is necessary to both to avoid additional damage at the injury site and to ensure actual therapeutic treatment. Skin temperatures should remain in the 40° C. to 45° C. range for optimum results. If the temperature falls below the optimum range, then the patient receives reduced benefit from the therapy. Conversely, if the temperature rises above the optimum range, then tissue damage (i.e., burns, redness, etc.) may occur if the pack is not removed quickly enough from the skin.

In the past, an easy and effective means for constantly monitoring the surface skin temperature during moist heat therapy has not been available to average consumer or to the professional therapist. Methods now in use for delivering moist heat lack a built-in means to determine whether the skin temperature is within the optimum therapeutic range. Therefore, the user, whether consumer or therapist, must continually remove the heat pack from the therapy site to accurately measure the skin temperature, thereby interrupting therapy. This approach is time-consuming and labor intensive, particularly when the patient is, for whatever reason (i.e., age, infirmity, etc.), not capable of utilizing the heat pack himself or herself. Alternatively, the user can depend upon past experience or rely upon the patient's comments about comfort levels. This method of gauging the skin temperature of another, however, is uncertain at best.

Surface skin temperature, however, may presently be monitored by thermocouples and monitoring equipment, but this method has significant drawbacks. First, the equipment is expensive. Second, such equipment is unavailable at the consumer level. Third, it is difficult to use, e.g., such equipment requires advanced skills to properly connect and is time consuming to apply. Further, the thermocouples create an intrusive effect on the therapy as well as act as a significant source of moisture and heat loss.

Therefore, there still exists a need in the art to provide a moist heat pack that provides a convenient, reliable means for continuously monitoring skin temperature at the therapy site without interrupting therapy. There also exists a need for a moist heat pack providing a barrier that prevents escape of moisture from the exposed surface thereby increasing the effectiveness of therapy.

Once an energized therapy pack (either hot or cold) is applied to the subject's injury, the surface skin temperature must be monitored. Maintaining an optimum range of temperature during therapy serves both to avoid additional damage at the injury site and to ensure actual therapeutic treatment. Devices currently in use for delivering temperature dependent therapy, whether hot or cold, lack a built-in means to continuously and conveniently determine whether the skin temperature is within the optimum therapeutic range during therapy.

Equally important, therefore, is the need in the art for a convenient and reliable temperature monitoring device for other temperature dependent therapeutic devices. Examples of such devices include cold therapy packs, electric heating pads, and the like.

SUMMARY OF THE INVENTION

The above disadvantages of the prior art are overcome by the present invention which provides an improved moist heat pack having a heat source positioned within its inner body portion, and a means on its top surface specifically calibrated for monitoring the temperature at the interface of the bottom surface of the heat pack and the subject's skin.

Thermal energy can be provided to the heat source by many methods, e.g., microwave stimulation, electric current and heating elements, hot/warm water activation, or by a exothermic chemical reaction of component materials of the heat source. One embodiment of the present invention provides a heat source comprised of a plurality of particulate beads that, when preheated by a source of thermal energy (e.g., microwave energy), absorb transmittable energy which, in turn, heats the skin during therapy.

The moist heat pack of the present invention may also provide a means for preventing moisture evaporation from the top of the moist heat pack. In one embodiment of the invention, the means for preventing moisture evaporation from the top of the moist heat pack is a water proof film of ethyl vinyl alcohol ("EVA") which can withstand successive microwavings without significant breakdown. The strategic placement of this insulator/barrier provides for improved heat and moisture retention by eliminating heat losses associated with evaporative cooling at exposed surfaces, which results in improved therapy at the injury site.

The present invention also provides an easy and effective means for continually monitoring the surface skin temperature during temperature dependent therapy without interrupting therapy. In a preferred embodiment of the present invention, the temperature monitoring device is a liquid crystal temperature indicating strip, calibrated to indicate the actual temperature at the interface of the bottom surface of the therapy pack and the subject's skin over a predetermined range of temperatures.

DESCRIPTION OF THE PREFERRED EMBODIMENTS

The present invention may be understood more readily by reference to the following detailed description of specific embodiments and the Example and Figures included therein.

As used in the claims, "a" means one or more.

Figure 1:
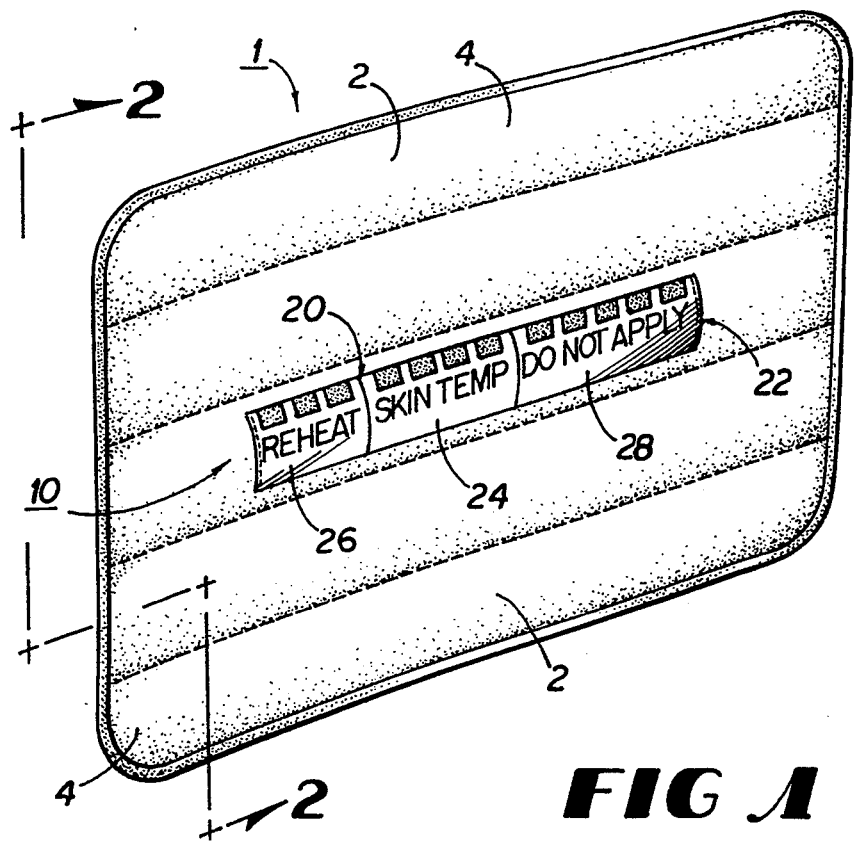
FIG. 1 is a perspective view of the microwavable moist heat pad.
Figure 2:
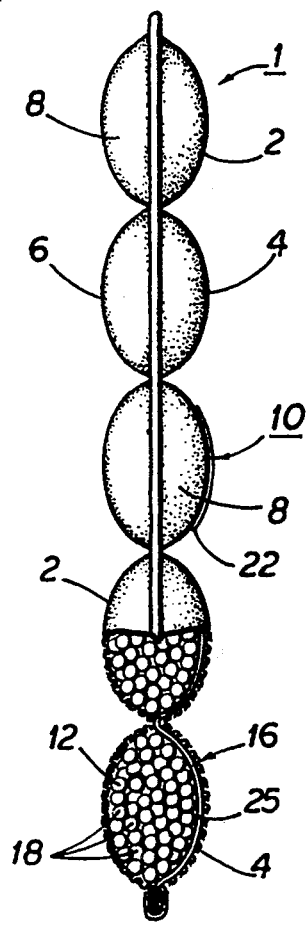
FIG. 2 is an end elevation partially sectioned as shown in FIG. 1 along lines 2—2.

Referring now to FIG. 1 and FIG. 2, one embodiment of the present invention, an improved moist heat pack 1 for applying moist heat therapy to a subject is shown. The moist heat pack 1 has an envelope 2 having a top surface 4, an opposite bottom surface 6, and an inner body portion 8 defined there between. The bottom surface 6 is the portion applied to the subject's skin (not shown). A heat source 12 is positioned in the inner body portion 8 of the envelope 2. The improved moist heat pack also has a temperature monitoring means 10 on the top surface 4 for monitoring the temperature at the interface of the bottom surface 6 of the envelope 2 and the subject's skin.

The heat source 12 can be selected from any of a number of sources including, but not limited to, microwave stimulation of microwavable susceptible material, electric current and heating elements, warm/hot water activation, or an exothermic chemical reaction of components of the heat source. In the presently preferred embodiment, as shown in FIG. 2, the heat source 12 of the moist heat pack 1 may comprise a plurality of particulate beads 18 that, when preheated by a source of thermal energy, absorb transmittable energy which heats the skin. For example, THERABEADS TM are reusable, microwave susceptible beads which serve as the heat source 12 in a presently preferred embodiment.

As shown in FIG. 2, the moist heat pack 1 may further comprise a means 16 for preventing moisture evaporation from the top surface 4. The means 16 for preventing moisture evaporation can be selected from any number of waterproofing barriers including vinyls, urethanes, and the like. In a presently preferred embodiment the moisture evaporation prevention means 16 is a water proof film of ethyl vinyl alcohol ("EVA") 25 located on the underside of the top surface 4 of the envelope 2.

As shown in the figures, the temperature monitoring means 10 comprises a temperature indicating means 20 calibrated to indicate the actual temperature at the interface of the bottom surface 6 of the envelope 2 and the subject's skin over a predetermined range of temperatures. The calibration of the temperature indicating means 20 is based upon a measure of the temperature at the top surface 4 of the envelope 2 adjusted for a determined width and density of the moist heat pack 1 and the determined coefficient of thermal energy transfer of the heat source 11.

The temperature monitoring means 10 may be a separate device that may be attached to any therapeutic pack. Examples of therapeutic packs include, but are not limited to, a moist heat pack, a cold therapy pack, or a heating pad. The temperature monitoring device is calibrated in a manner similar to the method described in the Example included herein.

The use of temperature sensing liquid crystal technology is known in the art. For example, thin film liquid crystal thermometers have been designed to measure and indicate the temperature of a thermal energy applied directly to the crystals. The temperature monitoring means 10 of one embodiment of the present invention utilizes the liquid crystal technology to indirectly measure temperature based upon specifically calibrated indices. Another use of liquid crystal technology in a health-care application is that shown by Flam, a co-inventor of the present invention, in U.S. Pat. No. 5,181,905. The Flam patent teaches a liquid crystal sensing device used on a dressing to monitor the healing of a wound, the hydration of a wound, or for aiding a recumbent patient in ascertaining susceptibility to the formation of a decubitus ulcer.

In a presently preferred embodiment, the temperature monitoring means 10 and the temperature indicating means 20 is a liquid crystal temperature indicating strip 22. The central zone 24 of the liquid crystal indicating strip 22 denotes skin temperature between 40° C. to the 45° C., which is the preferred skin temperature range for moist heat therapy. The liquid crystal indicating strip 22 has a subtherapeutic temperature range 26 beginning at temperatures marked below 40° C., which indicates a need to reheat the moist heat pack 1. A third zone 28 indicates temperatures above 45° C. This third zone 28 on the liquid crystal indicating strip 22 provides a warning to the user to remove the moist heat pack 1 from the subject's skin surface. One skilled in the art will appreciate that the calibration of the temperature indicating means 20 is dependent upon the selection of components for the envelope 2, the material selected as the heat source 12, and the presence or absence of the means 16 for preventing moisture evaporation.

The present invention also provides a method for monitoring skin surface temperature during the application of moist heat therapy to a subject. The method can utilize the embodiments as shown in FIGS. 1–2 having an envelope 2 having a top surface 4, an opposite bottom surface 6, an inner body portion 8 defined there between and a heat source 12 within the inner body 8. Specifically, the first step requires calibrating a temperature monitoring means 20 to indicate the actual temperature at the interface of the bottom surface 6 of the envelope 2 and the subject's skin over a predetermined range of temperatures.

The calibration is based upon a measure of the temperature at the top surface 4 of the envelope 2 adjusted for a preselected width and density of the moist heat pack 1 and the determined coefficient of thermal energy transfer of the heat source 12 as shown in the Example provided herein. Second, the method involves affixing on a moist heat pack 1, on the side opposite to the side applied to the skin (the bottom surface 6), a temperature monitoring device (e.g., the liquid crystal temperature indicating strip 22) specially calibrated to indicate skin surface temperature. Then, the method involves applying a thermal energy to the moist heat pack 1. The method then entails placing the moist heat pack 1 on the skin surface and observing the temperature monitoring device to ensure temperature remains within a predefined optimum range. As required, the method involves reapplying thermal energy to the moist heat pack 1 if the surface skin temperature falls below the optimum range or removing transmittable heat from the moist heat pack 1 if the surface skin temperature rises above the optimum range.

In addition, the present invention further provides a method for monitoring skin surface temperature during the application of moist heat therapy to a subject. The method utilizes the embodiments as shown in FIGS. 1–2 in applying moist heat therapy to a subject. In particular, the method involves applying thermal energy to the moist heat pack 1 and placing the moist heat pack 1 on the subject's skin surface. The method then entails observing the temperature monitoring device (the liquid crystal temperature indicating strip 22) to ensure temperature remains within a predefined optimum range as described herein. As required, the method involves applying thermal energy to the moist heat pack 1 if the surface skin temperature falls below the optimum range or removing transmittable heat from the moist heat pack 1 if the surface skin temperature rise above the optimum range.

The present invention is more particularly described in the following examples which are intended as illustrative only since numerous modifications and variations therein will be apparent to those skilled in the art.

EXAMPLES

The temperature monitoring strip of the present invention can be attached to the outer surface of a therapy pack to measure the surface skin temperature where it interfaces with the opposite or bottom side of the therapy pack. Calibration of the temperature monitoring strip is dependent upon the particular thermal characteristics of the therapy pack.

In this example, a moist heat pack was dimensioned to be approximately 12 inches by 12 inches. The outer envelope was formed from two pieces of polycotton sailduct. A moisture evaporation prevention means consisting of a water proof film of ethyl vinyl alcohol ("EVA") was applied to one piece of the polycotton sailduct. The two pieces were sewn together on three sides such that the EVA coating formed the underside of the top surface of the envelope. The inside of the envelope was then filled with THERABEADS ™ which acts as the heat source. The envelope was sewn closed and was further sewn together in equally spaced parallel pleats, thereby forming parallel rows of THERABEADS ™. At the thickest portion of the individual pleated rows, the distance from the top surface to the bottom surface was 1 inch.

Calibration of the liquid crystal temperature strip was accomplished by measuring and correlating heat transmission data collected from the top surface and skin surface. Experimental readings of the skin temperature were compared to the temperature readings at the top surface of the envelope during therapy. From this data, an equation was developed comparing the liquid crystal readings on the top surface (in degrees Fahrenheit) on the x-axis to average skin temperature (in degrees Fahrenheit) on the y-axis. In this example, the following equation resulted from the measurements:

$$y = 4517.4 - 115.03x + 0.99326x^2 - 0.0028398x^3.$$

With the equation, the liquid crystal temperature indicator strip was calibrated to indicate the skin surface temperature relative to the temperature of the top surface. Thus, when the moist heat pack is heated in a microwave and placed on the subject's skin, the temperature indicated by the liquid crystal strip is the temperature of the skin surface and not that of the top surface of the moist heat pack.

Although the present process has been described with reference to specific details of certain embodiments thereof, it is not intended that such details should be regarded as limitations upon the scope of the invention except as and to the extent that they are included in the accompanying claims.

What is claimed is:

1. An improved moist heat pack, comprising:
   a. an envelope having a top surface, an opposite bottom surface, and an inner body portion defined therebetween, the bottom surface being adapted to be applied to a subject's skin, thereby forming an interface therewith;
   b. a heat source positioned in the inner body portion of the envelope for applying moist heat therapy to the subject; and
   c. a means on the top surface for monitoring a temperature at the interface of the bottom surface of the envelope and the subject's skin while the bottom surface is in contact with the subject's skin.

2. The moist heat pack of claim 1, further comprising a means for preventing moisture evaporation from the top surface.

3. The moist heat pack of claim 2, wherein the moisture evaporation preventing means is a water proof film of ethyl vinyl alcohol ("EVA") located on an underside of the top surface of the envelope.

4. The moist heat pack of claim 1, wherein the heat source comprises a plurality of particulate beads that, when preheated by a source of thermal energy, absorb transmittable energy which heats the skin.

5. The moist heat pack of claim 1, wherein the temperature monitoring means comprises temperature indicating means calibrated to indicate an actual temperature at the interface of the bottom surface of the envelope and the subject's skin over a predetermined range of temperatures.

6. The temperature monitoring means of claim 5, wherein the temperature indicating means is a liquid crystal temperature indicating strip.

7. A therapeutic pack, comprising an envelope with a top surface and an opposite bottom surface and an inner body portion defined therebetween, the bottom surface being adapted to be applied to a subject's skin thereby forming an interface therewith, and means on the top surface for monitoring the temperature at the interface of the bottom surface of the envelope and the subject's skin while the pack is applied to the subject's skin.

8. The therapeutic pack of claim 7, wherein the therapeutic pack comprises temperature indicating means calibrated to indicate an actual temperature at the interface of the bottom surface of the envelope and the subject's skin over a predetermined range of temperatures.

9. The therapeutic pack of claim 8, wherein the temperature indicating means is a liquid crystal temperature indicating strip.

10. The therapeutic pack of claim 7, wherein the pack is selected from the group consisting of a moist heat therapy pack, a cold therapy pack, and a heating pad.

11. A method of making an improved moist heat pack, the moist heat pack being comprised of an envelope having a top surface, an opposite bottom surface, an inner body portion defined therebetween and a heat source within the inner body, the bottom surface being adapted to be applied to a subject's skin thereby forming an interface therewith comprising the steps of:
   a. calibrating a temperature monitoring means to indicate an actual temperature at the interface of the bottom surface of the envelope and the subject's skin over a predetermined range of temperatures while the pack is applied to the subject's skin; and
   b. affixing the temperature monitoring means to the too surface of the moist heat pack.

12. A method of applying moist heat therapy to a subject comprising:
   a. applying thermal energy to the moist heat pack of claim 1;
   b. placing the bottom surface of the moist heat pack on the subject's skin, thereby forming an interface therewith;
   c. observing the temperature monitoring means to ensure temperature at the interface remains within a predefined optimum range; and
   d. reapplying thermal energy to the moist heat pack if the surface skin temperature falls below the optimum range or removing transmittable heat from the moist heat pack if the subject's skin temperature rises above the optimum range.

* * * * *